United States Patent [19]

Kannagi et al.

[11] Patent Number: 5,173,420
[45] Date of Patent: Dec. 22, 1992

[54] MONOCLONAL ANTIBODY RECOGNIZING UN-NATURAL GANGLIOSIDE GD3

[75] Inventors: Reiji Kannagi; Yoshiko Kirihata, both of Kyoto; Tomoya Ogawa, Musashino; Masaaki Numata, Kawagoe; Mamoru Sugimoto, Tokyo, all of Japan

[73] Assignee: MECT Corporation, Tokyo, Japan

[21] Appl. No.: 310,654

[22] Filed: Feb. 15, 1989

[30] Foreign Application Priority Data

Feb. 19, 1988 [JP] Japan .................................. 63-37068

[51] Int. Cl.$^5$ ......................... C12N 5/20; C07K 15/28
[52] U.S. Cl. .................. 435/240.27; 435/70.21; 435/172.2; 530/387.5; 530/388.8
[58] Field of Search ..................... 530/387, 388, 387.5, 530/388.8; 435/70.21, 172.2, 240.27; 536/17.2, 17.4, 17.9

[56] References Cited

FOREIGN PATENT DOCUMENTS 91005 12/1983 European Pat. Off. .
254105 1/1988 European Pat. Off. .
267615 5/1988 European Pat. Off. .
8802773 4/1988 World Int. Prop. O. .

OTHER PUBLICATIONS

Handbook of Experimental Immunology, vol. 4, Applications of Immunological Methods in Biological Science., pp. 117.1–117.20, 1986, Kannagi et al: Monoclonal antibodies directed to . . .

The Journal of Biological Chemistry, vol. 250, No. 5, Mar. 10, 1975, pp. 1926–1932, Bhattacharjee et al: Structural Determination of Sialic Acid Polysaccharide Antigens of Neisseria meningitidis Serogroups B and C . . .

The Journal of Biological Chemistry, vol. 260, No. 11, Jun. 10, 1985, pp. 6623–6631, Fukuda et al: Embryonal Lactosaminoglycan.

Nudelman et al., "Characterization of a Human Melanoma-Associated Ganglioside Antigen Defined by a Monoclonal Antibody, 4.2," J. Biol. Chem 257:12752–12756, 1982.

Fukuda et al., "Embryonal Lactosaminoglycan," J. Biol. Chem. 260: 6623–6631, 1985.

*Primary Examiner*—John J. Doll
*Assistant Examiner*—Robert D. Budens
*Attorney, Agent, or Firm*—Oblon, Spivak, McClelland, Maier & Neustadt

[57] ABSTRACT

A monoclonal antibody A exhibits specificity to the sialic acid glycolipid containing the epitope NeuAcα2→9NeuAc terminal. A monoclonal antibody B exhibits specificity to the sialic acid glycolipid containing the epitope NeuAcα2→6Galβ terminal. A monoclonal antibody C exhibits specificity to the sialic acid glycolipid containing at least one epitope selected from the group of NeuAcα2→9NeuAc terminal, NeuAcα2→6Galβ terminal and NeuAcα2→1Cer. Hybridomas are prepared which produce antibodies A, B and C. A process for producing the hybridomas is disclosed including the step of fusing a myeloma cell and a B cell (lymphocyte) produced by the immunization of animal using as an antigen, the sialic acid glycolipid containing at least one epitope of the group NeuAcα2→9NeuAc terminal, NeuAcα2→6Galβ terminal and NeuAcα2→1Cer.

6 Claims, 2 Drawing Sheets

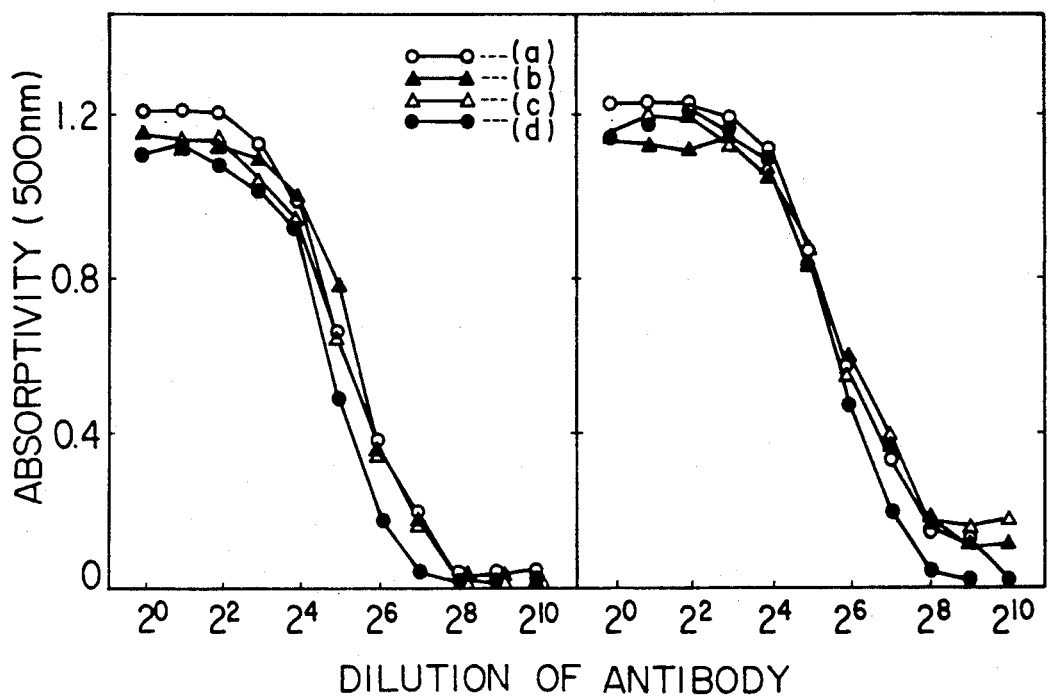
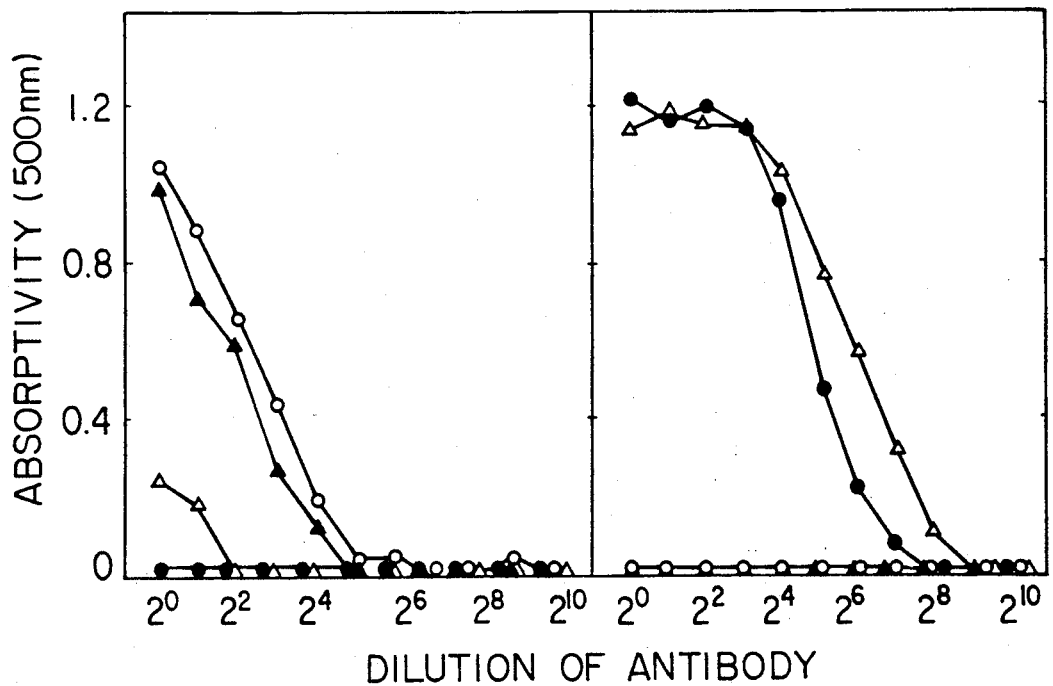

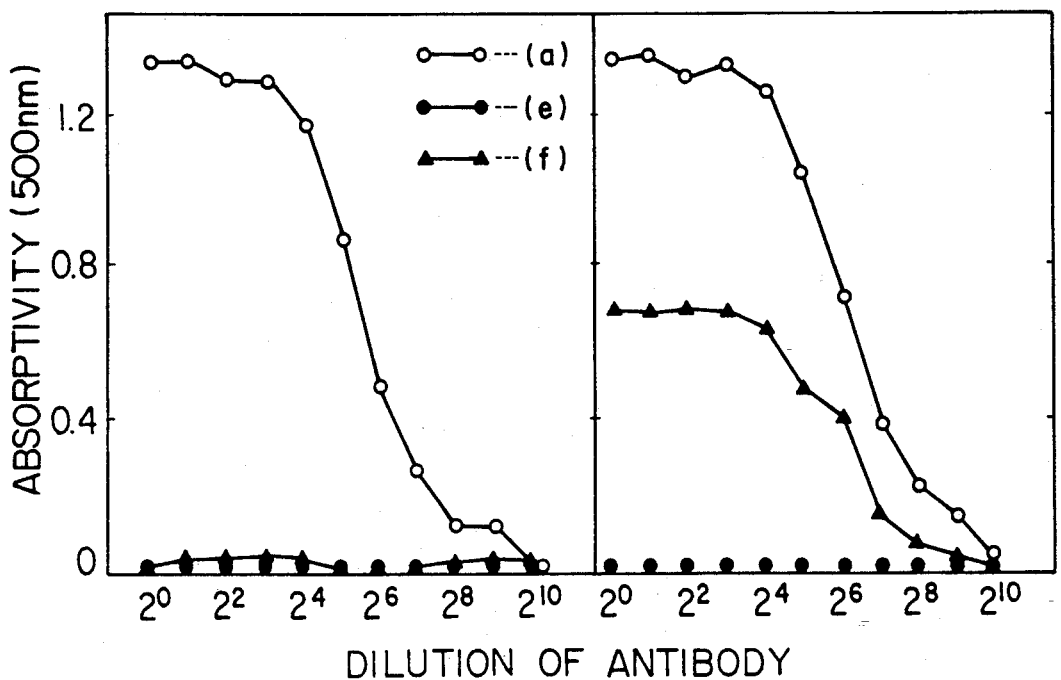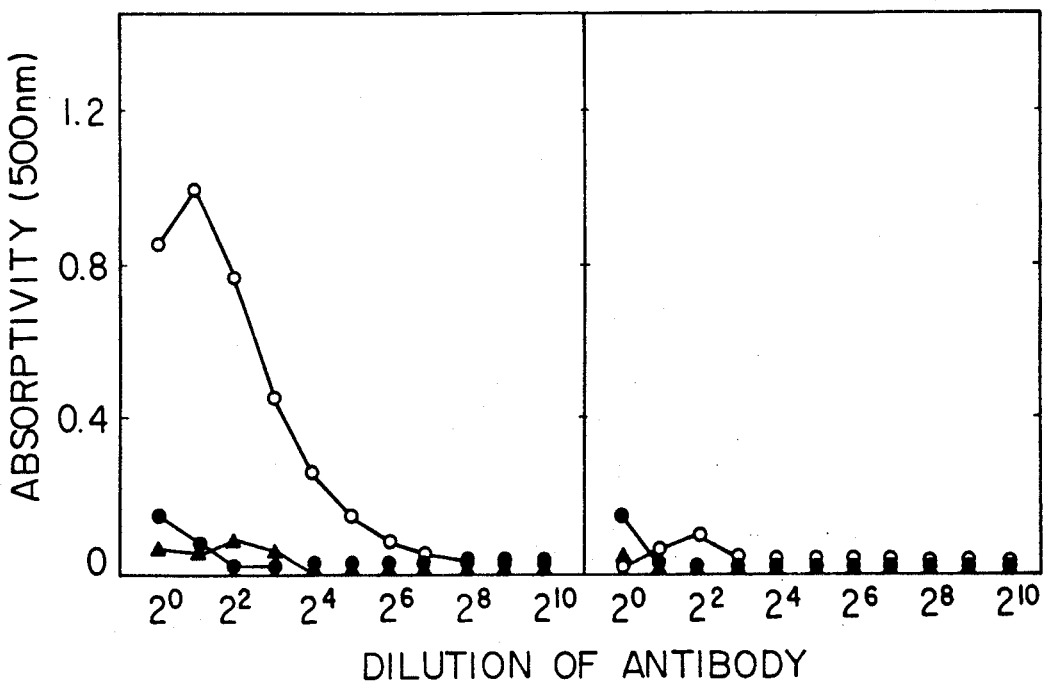

MONOCLONAL ANTIBODY RECOGNIZING UN-NATURAL GANGLIOSIDE GD3

BACKGROUND OF THE INVENTION

1. Field of the Invention

The present invention relates to novel hybridomas, a process for producing the same and anti-sialic acid glycolipid monoclonal antibodies produced by the aforementioned process.

2. Prior Art

Recent progress in the study of monoclonal antibodies shows that sugar chain antigens, particularly glycolipid antigens, exhibit strong carcinogenic properties. An effective measure for the diagnosis and medical treatment of cancers is thus thought to be the establishment of monoclonal antibodies to glycolipid antigens. However, some glycolipids are present in natural substances in such small amounts as to make it difficult to obtain the refined glycolipids required for the establishment of monoclonal antibodies. In addition, there are some glycolipids whose existence is theoretically anticipated, though they have never been isolated. One possible method for producing monoclonal antibodies to such glycolipid antigens is that of producing the antibodies while artificially synthesizing the corresponding glycolipids. There are also sugar chain antigens which are significant as carcinogens and known to be present in glycoproteins but which have never been found in glycolipids. It is also known that the production efficiency of monoclonal antibodies to such sugar chain antigens is extremely low when they are produced by immunizing glycoproteins, and thus it is expected that the antibodies could be produced more easily by synthesizing glycolipids having the same sugar chains and using the thus synthesized glycolipids as immunization sources. This is because the process for the preparation of monoclonal antibodies to glycolipids is now well established while the process for the preparation of antibodies to glycoproteins has not yet been established. Accordingly, in view of the present state of the related technologies, there is a continued need for a novel process for the preparation of monoclonal antibodies to rare antigens, such as cancer-associated glycolipid antigens, and for monoclonal antibodies per se produced thereby.

SUMMARY AND OBJECT OF THE INVENTION

An object of this invention is to provide novel hybridomas which produce monoclonal antibodies to carcinogenic glycolipid antigens.

Another object of this invention is to provide a process for the preparation of such hybridomas.

A further object of this invention is to provide anti-sialic acid glycolipid monoclonal antibodies produced by the process as described above.

More specifically, we have tried to chemically synthesize ganglioside NeuAc$\alpha$2→9NeuAc$\alpha$2→6Gal$\beta$1→4Glc$\beta$1→1Cer, a sort of glycolipid antigen, and to establish a monoclonal antibody to the ganglioside, and have succeeded in obtaining several monoclonal antibodies. This invention was thus accomplished.

Accordingly, the present invention provides a monoclonal antibody (hereinafter referred to as antibody A) exhibiting specificity to the sialic acid glycolipid containing, as an epitope (antigen determination group), NeuAc$\alpha$2→9NeuAc terminal. Also provided according to the invention is a monoclonal antibody (hereinafter referred to as antibody B) exhibiting specificity to sialic acid glycolipid containing, as an epitope (antigen determination group), NeuAc$\alpha$2→6Gal$\beta$ terminal. Further provided according to the invention is a monoclonal antibody (hereinafter referred to as antibody C) exhibiting specificity to sialic acid glycolipid containing at least one epitope (antigen determination group) selected from the group consisting of NeuAc$\alpha$2→9NeuAc terminal, NeuAc$\alpha$2→6Gal$\beta$ terminal and NeuAc$\alpha$2→1Cer. The present invention further relates to a hybridoma which produces the antibody A, the antibody B or the antibody C. The present invention still further relates to a process for producing a hybridoma characterized by effecting cell fusion between a myeloma cell and a B cell (lymphocyte) produced by immunization of an animal while using, as an antigen, a sialic acid glycolipid containing at least one epitope selected from the group consisting of NeuAc$\alpha$2→9NeuAc terminal, NeuAc$\alpha$2→6Gal$\beta$ terminal and NeuAc$\alpha$2→1Cer.

DESCRIPTION OF THE DRAWINGS

The invention will now be described in detail with reference to preferred embodiments explained in conjunction with the appended drawings in which:

FIGS. 1 (i) to 1 (iv) are graphs showing specificities of monoclonal antibodies to antigens determined by the enzymatic antibody test; and FIGS. 2 (v) to 2 (viii) are graphs showing specificities of monoclonal antibodies to antigens determined by the enzymatic antibody test.

DESCRIPTION OF THE INVENTION

The present invention will now be described in detail

The hybridoma of the invention can be prepared through the Method of Keller and Milstein et al., namely by immunizing an animal with the corresponding antigen to obtain B cell (lymphocyte) which is then fused with myeloma cell. The term "antigens" used throughout this specification means sialic acid glycolipids each containing at least one epitope selected from the group consisting of NeuAc$\alpha$2-9NeuAc terminal, NeuAc$\alpha$2→6Gal$\beta$ terminal and NeuAc$\alpha$2→1Cer, preferably ganglioside NeuAc$\alpha$2→9NeuAc$\alpha$2→6Gal$\beta$1→4Glc$\beta$1→1Cer (Un-natural GD$_3$).

Each of the monoclonal antibodies produced by the hybridomas according to this invention recognizes at least one of NeuAc$\alpha$2→9NeuAc terminal, NeuAc$\alpha$2→6Gal$\beta$ terminal and NeuAc$\alpha$2→1Cer as an epitope (antigen determination group) amongst the aforementioned ganglioside glycolipids, and exhibits specific behavior. Accordingly, the monoclonal antibodies produced by the hybridomas according to the invention exhibit high level specificities to any of the sialic acid glycolipids so long as they contain one or more of the aforementioned epitopes. There is no particular restriction on animal species, the only requirement being that the animal have these sialic acid glycolipids to provide specificity to monoclonal antibodies of the invention.

Immunization against the aforementioned sialic acid glycolipids acting as antigens can be carried out in rabbit, human being, mouse, rat or almost any other animal. Among these animals, the mouse is preferable, the most preferable being the Balb/c mouse. The thus-produced B cell (lymphocyte) is a cell producing the corresponding monoclonal antibody of the invention, and spleen cells are preferably used.

On the other hand, the "myeloma cell" can be almost any myeloma cell originating from a variety of animals, for example human being, mouse, rat and rabbit. The myeloma cell originating from the mouse is preferable the most preferable being the X63-Ag8.653 myeloma cell originating from the Balb/c mouse. These myeloma cells have active multiplication capacities for producing monoclonal antibodies from the hybridoma (Deposition Nos. HB 9473, HB 9474 and HB 9551 deposited Apr. 8, 1987, Apr. 8, 1987 and Apr. 16, 1987, respectively at the American Type Culture Collection (ATCC), Rockville, Md., USA of the invention which are produced by cell fusion with the aforementioned B cells.

The process for the production of the hybridomas, according to this invention, will now be described.

Initially, a mouse is immunized by inoculating one of the aforementioned antigens, for example ganglioside NeuAc$\alpha$2 →9NeuAc$\alpha$2→6Gal$\beta$1→4Glc$\beta$1→1Cer, through muscular, subcutaneous or intra-peritoneal inoculation, preferably through intra-peritoneal inoculation, of the antigen. During this immunization operation, an incomplete or complete adjuvant may be used as an immunization promotor, examples of such adjuvants being oils, emulsifiers, fertilized tubercular bacillus, fertilized Salmonella bacillus and mixtures thereof, and the preferable adjuvant being fertilized Salmonella minnesota. It is preferable to use the antigens and adjuvants in the form of solutions resembling a physiological saline solution, such as a solution in a physiological saline solution buffered with phosphates.

The animals used for immunization should preferably be phylogenically distant from the animals from which the antigens used are obtained, since animals have low auto-immune sensitivity. However, in order to avoid such difficulty, immunization in vitro can be performed.

The B cell obtained through the procedure as described above is then subjected to cell fusion with a myeloma cell.

Polyethylene glycol, HVJ or like may be used as the fusing agent. Polyethylene glycol 4000 is preferable.

It is preferable to use an HAT medium in order to select the hybridoma cells. Subsequently, the hybridomas are subjected to a cloning process, for example, methyl cellulose processing, soft agarose processing or limiting dilution processing, to produce antibodies in these cells.

The antibody activities of the thus produced monoclonal antibodies are measured by an ordinary method of selecting and saving the hybridomas having high antibody activity.

The monoclonal antibodies produced by the hybridomas of the invention may be used for detecting naturally existing glycolipid antigens in cancer tissue of human beings or animals Accordingly, the monoclonal antibodies of the invention may be used in common processes, such as ELISA or RIA, for detecting cancer-related ganglioside glycolipids. In addition, the monoclonal antibodies of the invention may be used in affinity chromatography to separate combined antigens Further, monoclonal antibodies labeled with radioactive isotopes may be used for the detection of tumors or detection of localized tumor, and also may be used at high dosages for the treatment of tumors. Furthermore, the monoclonal antibodies of the invention may be bonded to various chemotherapeutic agents to increase their toxicity to cancer cells. It is also possible to use the monoclonal antibodies of the invention for medical treatment or diagnostic testing for the presence of the antigens in animals, including human beings, mice and other animals.

EXAMPLES OF THE INVENTION

A preferred embodiment of the invention will now be described hereinbelow to provide a better understanding of the invention.

(A) Preparation of Sample (1) Preparation of Ganglioside NeuAc$\alpha$2→9NeuAc$\alpha$2→6Gal$\beta$1→4Glc$\beta$→1Cer (Compound (a))

The Compound (a) was prepared through the process as shown by the preparation process diagram set forth below. Details of the process will be found in the specification of Japanese Patent Application No. 157647/1986 which will be incorporated herein as a reference.

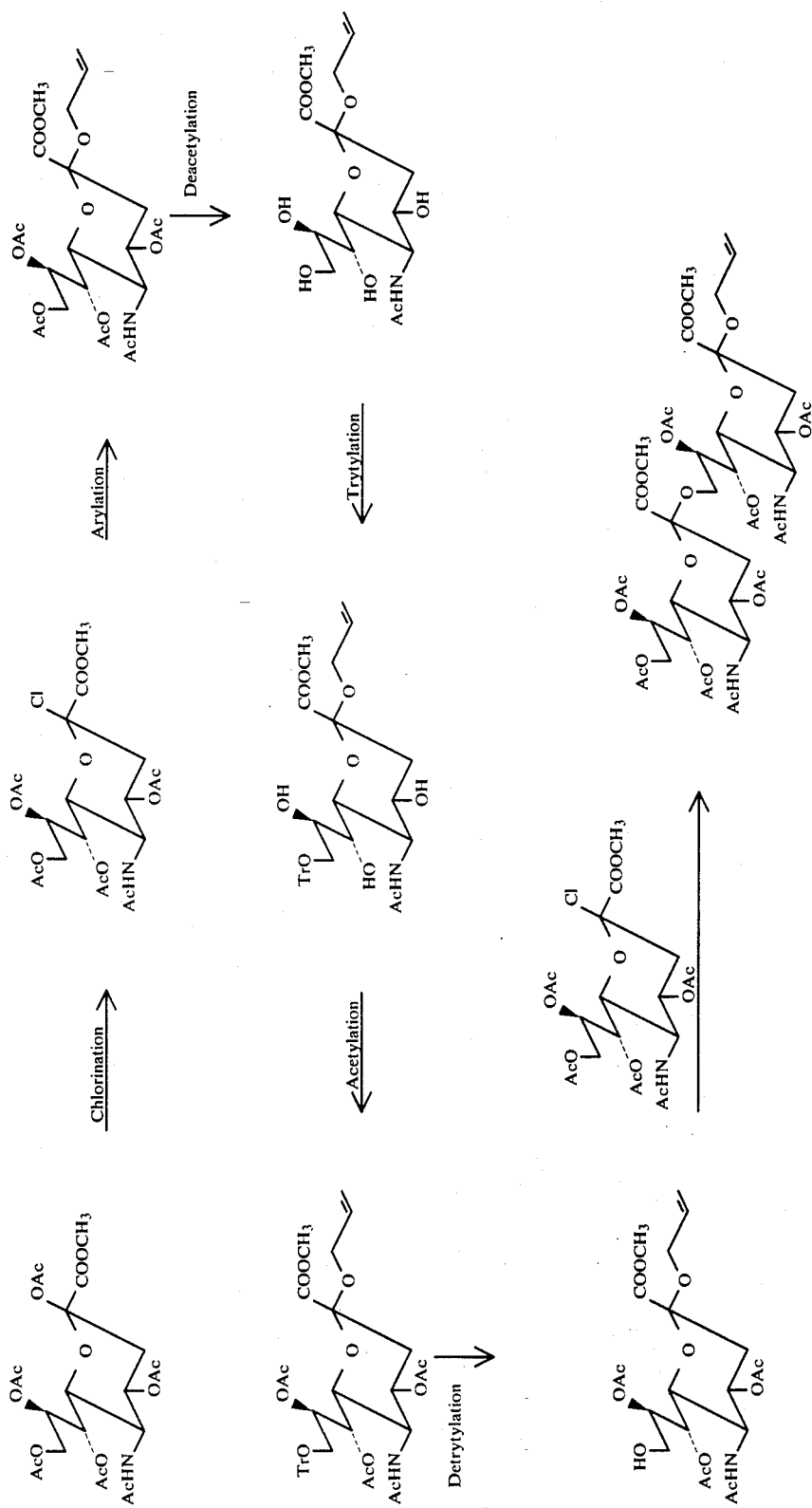
Preparation Process Diagram

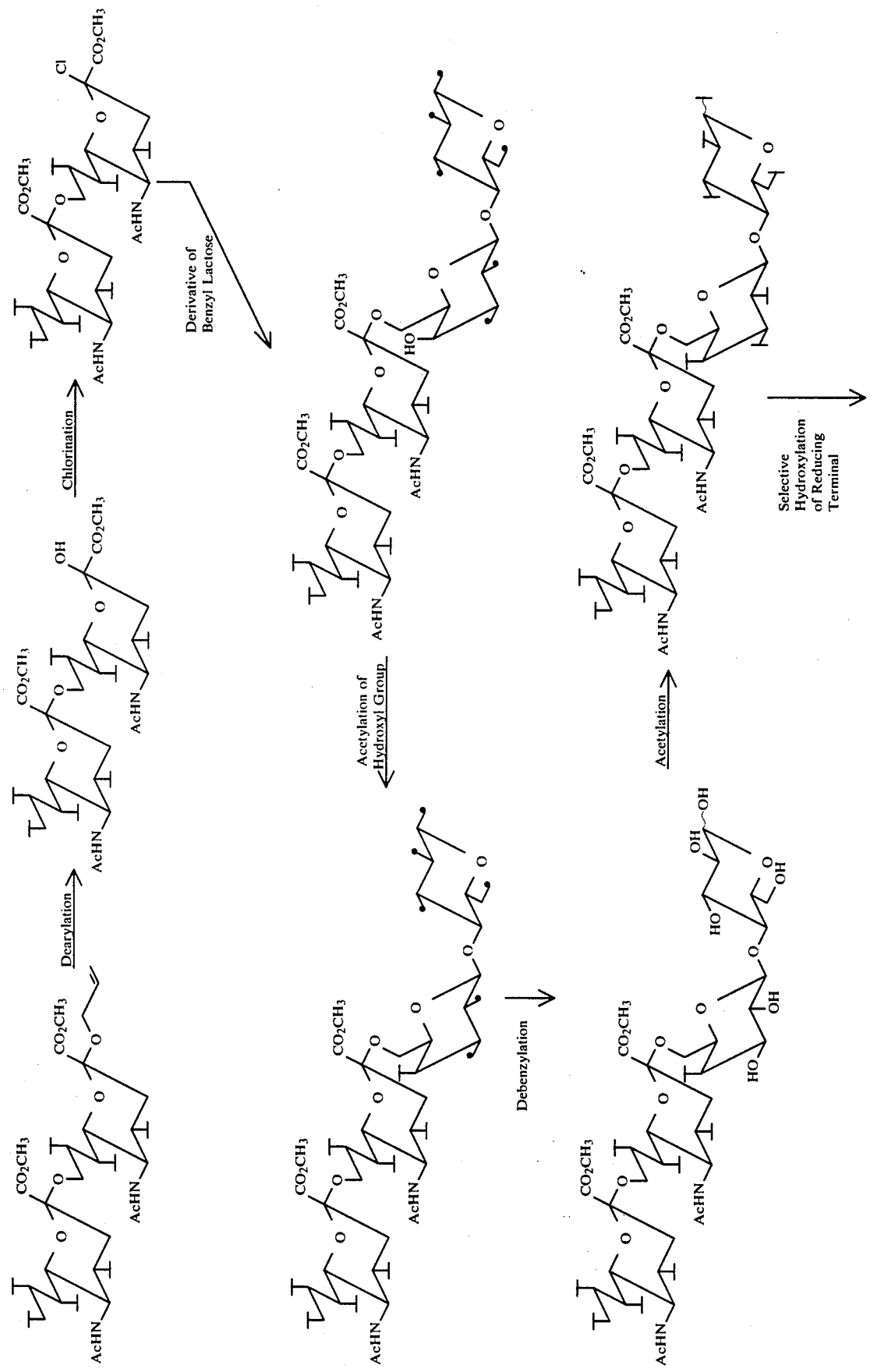

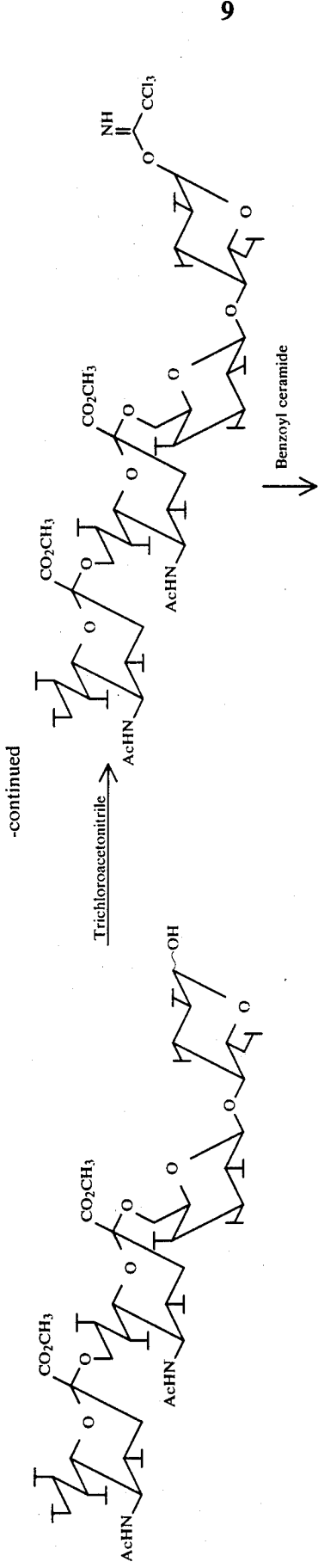
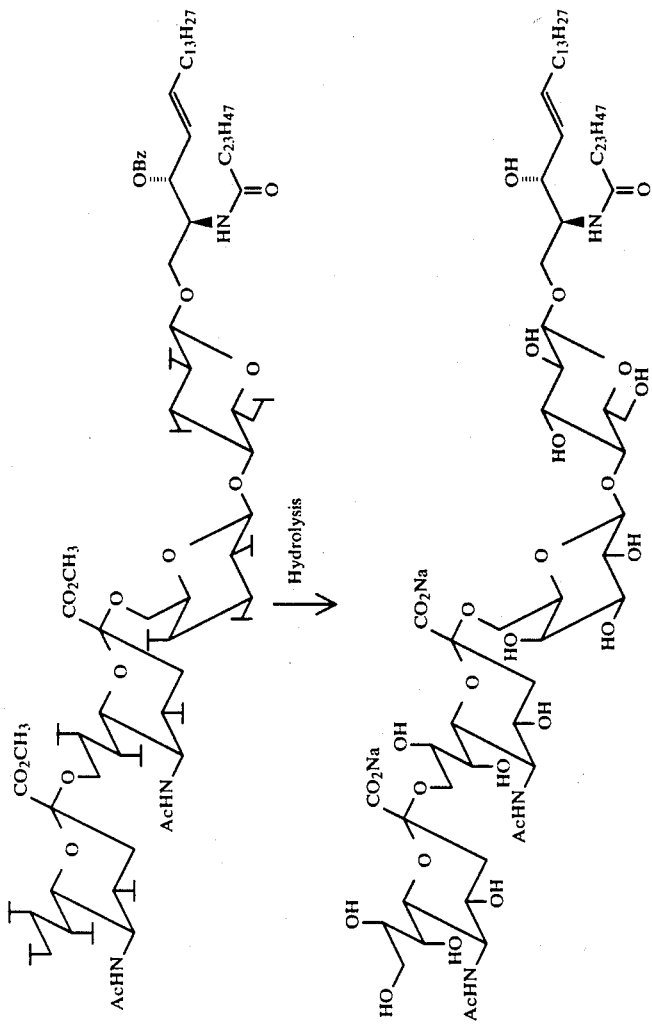

(2) Preparation of Antigen Solution

One milligram of the chemically synthesized Compound (a) was added to 200 μl of ethanol and mixed with 0.8 ml of an adjuvant solution containing 4 mg of Salmonella minnesota R595 which had been treated with acetic acid, incubated for 50 minutes in an aqueous solution maintained at 50° C. and then dissolved in a physiological saline solution buffered with phosphate (PBS(−), Ca and Mg being removed), whereby an antigen solution was prepared (3) Animal Used in Experiment Female Balb/c mouse aged six weeks was used in the experiment and bled under normal conditions.

(4) Culture Medium

RPMI culture medium (Nissui (2) RPMI-1640) was used in the experiment. The culture medium was adjusted to contain 50 μg/ml (final concentration) of kanamycin sulfate and 10% of calf fetal serum (FBS), and cultivation was effected at 37° C. for 24 hours in the presence of 5% $CO_2$.

In another experiment, HAT culture medium was used. An amount of 0.0388 gram of thymidine and 0.1361 gram of hypoxanthine were dissolved in 100 ml of distilled water by heating, and the solution was reserved as a storage solution of 100 times concentration. Similarly, 0.0176 gram aminopterin was dissolved in 100 ml of distilled water with the addition of a small amount of a 1N aqueous solution of sodium hydroxide, with subsequent dilution to ten times volume with RPMI-1640 culture medium. The resulting solution was kept as a storage solution of 100 times concentration at −(minus) 20° C. as shielded from light. In use, HAT culture medium was prepared by adding respective storage solutions to the FBS-containing RPMI-1640 culture medium each in a ratio of 1/100.

HT culture medium was used in a further experiment, the HT culture medium being prepared by adding only the storage solution containing thymidine and hypoxanthine in a ratio of 1/100. Generation of mutants was inhibited by adding 6-thioguanine so that the solution contained 3 μg/ml of 6-thioguanine.

(B) Preparation of Hybridoma (1) Immunization Process

The aforementioned mouse was immunized by intraperitoneally inoculating said antigen solution in amounts of 5 μg at the initial stage, 15 μg on the fourth day, 20 μg on the seventh day, 25 μg on the twelveth day and 35 μg on the 26th day. After the fifth inoculation, spleen cell lymphocytes were extracted from the immunized mouse, and a suspension of single cells was prepared.

(2) Cell Fusion Process

Cell fusion of the thus obtained spleen cell lymphocytes and mouse myeloma cells was effected in accordance with the Kohler & Milstein Method. Specifically, $1 \times 10^8$ cells of the spleen cell lymphocyte were fused with $1 \times 10^7$ of myeloma cells in the presence of 50% polyethylene glycol (PEG 4000) in the RPMI-1640 culture medium deprived of the serum.

(3) Selection and Propagation of Hybridoma

After the completion of cell fusion, the fused cell was cultured in the HAT culture medium (containing hypoxanthine, aminopterin and thimidine) at 37° C. in an atmosphere of 5% $CO_2$.

(C) Appraisal of the Reactivity between Monoclonal Antibody and Ganglioside Glycolipid Hybridomas exhibiting antibody activities to Compound (a) were subjected to cloning to obtain hybridomas which were subjected to enzymatic antibody test to determine the reactivities thereof with the ganglioside glycolipids (a) to (f) set forth below.

(a) NeuAcα2→9NeuAcα2→6Galβ1→4Glcα1→1Cer
(b) NeuAcα2→9NeuAcα2→1Cer
(c) NeuAcα2→6Galβ1→4Glcβ1→1Cer
(d) NeuAcα2→6Galβ1→4GlcNAcβ1→3Galβ1→4Glcβ1→1Cer
(e) NeuAcα2→3GAllβ1→4GlcNAcβ1→3Galβ1→4Glcβ1→1Cer
(f) NeuAcα2→1Cer (1) Enzymatic Antigen Test (ELISA Test)

A plane plate having 96 wells (produced by Falcon Corp.) was pre-treated with ethanol and then used in the following experiment. The wells of the plate was filled with 20 μl of respective ethanol solutions of glycolipids having an optimal concentration of 50 μg/ml, followed by evaporation of the solvent and then addition of 100 μl of a 1% egg alubumin PBS(−) solution, and allowed to stand at room temperature for 30 minutes. After removing the solution by shaking the plate upside down, 50 μl of primary antibody was added to each well and the plate was allowed to stand at room temperature for an hour and 30 minutes. The primary antibody was then removed similarly as the preceding step and each well was rinsed three times with 150 μl of the PBS(−) solution, 100 μl of a 1% egg white albumin PBS(−) solution was added, followed by standing for 30 minutes. After removing the solution added in the preceding step, 50 μl of a secondary antibody diluted to have an optimal concentration with a 1% egg white alubumin PBS(−) solution was added, and then the plate was allowed to stand at room temperature for an hour and 30 minutes. Similarly as for the primary antibody, each well was rinsed with the PBS(−) solution three times and then 100 μl each of reaction solution was poured into the respective wells to allow the reaction to proceed in a dark place. The reaction solution used in the experiment was prepared by adding orthophenylenediamine and hydrogen peroxide to a citric acid/phosphoric acid buffer (pH=5) so that the final concentration of the former was adjusted to 0.4 mg/ml and the final concentration of the latter was adjusted to 0.01%. The reaction was stopped by adding 30 μl of a 8N sulfuric acid solution, and then colorimetric determination was conducted at an absorption wave length of 500 nm. The primary antibodies used were hybridoma culture solutions or monoclonal antibodies, and the secondary antibody used was goat anti-mouse IgG.M.A antibody labeled with horseradish peroxidase (HRP).

The results of reactions between the monoclonal antibody in the culture medium for the hybridoma and the ganglioside glycolipids denoted by (a) to (f) are shown in FIGS. 1(i) to 1(iv) and FIGS. 2(v) to 2(viii). FIGS. 1(i) and FIG. 2(vi) show the results found for the same monoclonal antibody; FIG. 1(ii) and FIG. 2(vi) show the results found for the same monoclonal antibody; and FIG. 1(iii) and FIG. 2(vii) show the results found for the same monoclonal antibody. FIG. 1(iv) and FIG. 2(viii) show the results of comparison experiments in which a monoclonal antibody exhibiting specificity to NeuAcα2→6Galβ originating from a natural glycolipid was used to determine the reaction specificities thereof with the compounds (a) to (d).

As will be apparent from FIGS. 1 and 2, the monoclonal antibody (Hybridoma Deposition No. HB 9473 (ATCC)) shown in FIG. 1(i) and FIG. 2(v) is the antibody B of the invention since it recognizes the NeuAcα2→9NeuAc terminal and/or NeuAcα2→6Galβ terminal as an epitope. Likewise, the monoclonal antibody shown in FIG. 1(ii) and FIG. 2(vi) is the antibody C (Hybridoma Deposition No. HB 9474 (ATCC)) of the invention since it recognizes at least one epitope selected from the group consisting of NeuAcα2→9NeuAc terminal, NeuAcα2→6Galβ terminal and NeuAcα2→1Cer. It should be appreciated from the foregoing that the monoclonal antibody C of the invention exhibits specificity over a wide range while exhibiting cross reactivity of some extent with various natural and synthesized glycolipids have resembling structures. On the other hand, it is found that the monoclonal antibody (Hybridoma Deposition No. HB 9551 (ATCC)) shown in FIG. 1(iii) and FIG. 2(vi) is the monoclonal antibody A of the invention since it recognizes NeuAcα2→9NeuAc terminal as an epitope.

It can thus be understood that the monoclonal antibody C, according to the invention, exhibits cross reactivity of some extent with various natural and synthesized glycolipids in a wider range. It is believed that this is because each of the sugar chain antigens has plural overlapping antigen epitopes on the molecular surface, causing it to exhibit complicated immunization responses.

What is claimed is:

1. A hybridoma cell line having all the identifying characteristics of the hybridoma having ATCC accession No. HB 9551.

2. A monoclonal antibody produced by the hybridoma having ATCC accession No. HB 9551 exhibiting specificity to a sialic acid glycolipic containing the epitope designated NeuAcα2→9NeuAc terminal.

3. A hybridoma cell line having all the identifying characteristics of the hybridoma having ATCC accession No. HB 9473.

4. A monoclonal antibody produced by the hybridoma having ATCC accession No. HB 9473 exhibiting specificity to a sialic acid glycolipid containing the epitope designated NeuAcα2→9NeuAc Terminal or the epitope designated NeuAcα2→6Galβ terminal.

5. A hybridoma cell line having all the identifying characteristics of the hybridoma having ATCC accession No. HB 9474.

6. A monoclonal antibody produced by the hybridoma having ATCC accession No. 9474 exhibiting specificity to a sialic acid glycolipid containing the epitope designated NeuAcα2→9NeuAc terminal, the epitope designated NeuAcα2→6Galβ terminal or the epitope designated NeuAcα2→1Cer.

* * * * *